United States Patent [19] [11] Patent Number: 4,588,685
Knoll et al. [45] Date of Patent: May 13, 1986

[54] PROCESS FOR THE PREPARATION OF A NEW-TYPE ACTIVE SUBSTANCE SELECTIVELY INHIBITING FOOD INTAKE

[75] Inventors: József Knoll, Budapest; Janós Nagy, Szentendre; Huba Kalasz; Berta Knoll, both of Budapest, all of Hungary

[73] Assignee: Richter Gedeon Vegyeszeti Gyar Rt., Budapest, Hungary

[21] Appl. No.: 632,439

[22] Filed: Jul. 19, 1984

[30] Foreign Application Priority Data

Jul. 29, 1983 [HU] Hungary .................. 2718/83

[51] Int. Cl.$^4$ .................................. C12P 21/06
[52] U.S. Cl. .................................. 435/69; 435/68; 424/101; 514/2; 514/8; 530/380; 530/414; 530/830
[58] Field of Search ............ 424/101; 435/68, 69

[56] References Cited

U.S. PATENT DOCUMENTS 4,294,825 10/1981 Knoll et al. .................. 424/177
4,430,264 2/1984 Knoll et al. .

Primary Examiner—Sam Rosen
Attorney, Agent, or Firm—Karl F. Ross; Herbert Dubno

[57] ABSTRACT

The invention involves isolating a food intake suppressant by subjecting blood serum to ultrafiltration transmitting up to a molecular weight of 30,000 daltons, partially evaporating the filtrate, removing the insoluble part from the concentrate obtained, adding trichloroacetic acid up to a concentration of 5 to 25 weight-/volume percent to the liquid phase at a temperature of 0° to 10° C., removing the proteins precipitated, subjecting the obtained solution to chromatography on a gel with a void volume below a molecular weight of 4000 daltons, eluting with a solution of pH 6.0 to 7.0, concentrating the biologically active fractions, chromatographing again on a gel with a void volume below a molecular weight of 4000 daltons, fractionating by elution with water, lyophilizing the active fractions, dissolving the lyophilized fractions in a buffer of pH 8.1 to 8.2, adding trypsin and chymotrypsin to the solution in a substantially identical amount of 0.01 to 0.2 by weight as calculated for the total weight of the lyophilized product, subjecting the mixture to digestion at a temperature of 36° C. to 39° C., preferably with occasionally shaking from 20 to 30 hours, adding after the first 5 hours trypsin and chymotrypsin in a substantially half amount as calculated for the original enzyme quantity and continuing the digestion, then adding trichloroacetic acid to the reaction mixture up to a concentration of 4 to 6 weight/volume percent at a temperature between 0° and 10° C., keeping the mixture at a temperature between −15° C. and 5° C. for 1 to 24 hours, removing the insoluble part, subjecting the reaction mixture to chromatography on a gel with a void volume below a molecular weight of 4000 daltons, fractionating by elution with water and lyophilizing the biologically active fractions.

9 Claims, 2 Drawing Figures

PROCESS FOR THE PREPARATION OF A NEW-TYPE ACTIVE SUBSTANCE SELECTIVELY INHIBITING FOOD INTAKE

FIELD OF THE INVENTION

The present invention relates to a process for preparing an appetite suppressant.

BACKGROUND OF THE INVENTION

In the Hungarian patent specification No. 178,703 (see U.S. Pat. No. 4,294,825) a process has been described for the preparation of a selective anorexogenic substance, i.e. of a product selectively inhibiting the food intake. This substance, which had not been known so far and operated by a new mode of action was prepared from the human plasma and called satietin. It was a partially purified product by far exceeding, however, the activity of similarly acting agents known so far.

The product was purified by ultrafiltration of the plasma and by using a two-step chromatography on Sephadex G-15 and Bio-Gel P-2 gels.

The peptide nature of the substance was determined as well as the quantitative relations of the aminoacids. In addition to the aminoacids, sugar constituents were also found after hydrolysis; thus, this substance acting specifically on the satiety centre was thought to be a glycoprotein.

It had been found by developing the invention that the active fraction could further be resolved, i.e. purified by an additional process. According to the Hungarian patent application No. 2783/81 as modified on 03/03/1982 (see U.S. Pat. No. 4,430,264), a product was obtained which was 3 to 4 times more effective and the chemical composition of which significantly differed from that of the active substance obtained by the process mentioned above. This product could be considered as a chemically pure, uniform, homogeneous active substance. Its physical characteristics and ultimate composition were also determined.

According to the above-mentioned process, the plasma was subjected to an important operation after ultrafiltration; namely, the plasma filtrate was treated with trichloroacetic acid to remove the present serum proteins (albumin, etc.), a defined part of which could pass the Amicon membrane. After the treatment with trichloroacetic acid, the precipitated serum proteins were settled by centrifuging and the pure supernatant containing the biologically effective satietin fractions were further purified on gel columns. In the first step, an ammonium acetate buffer was used for elution from a Sephadex G-15 column, the fractions containing the activity were collected at the void volume and desalted on a Bio-Gel P-2 column after an appropriate concentration. The salt-free fractions could be considered as a substance of high purity, thus, this product was quite useful for the biological study involving all experiments on food intake.

In this step, only peptides and glycopeptides of lower molecular weight remained which had no influence on the satietin activity and were in turn removed by electrophoresis and affinity chromatography. The pure active substance was obtained by lyophilization after fractionating by affinity chromatography on a Con-A Sepharose column and repeated desalination on a Bio-Gel P-2 column. The substance obtained in this way proved to be a glycoprotein with a low peptide (5 to 25%) and a high carbohydrate (60 to 90%) content. The molecular weight of the active substance was in the range of 50,000 to 70,000 daltons, while its isoelectric point was found to be neutral, namely the pI was 7.0 to 7.1.

SUMMARY OF THE INVENTION

Now it has been found in the course of our recent investigations that the above-mentioned known process can significantly be simplified. By inserting a particular step, a substance selectively inhibiting the food intake could be obtained with different physical properties. This substance was chemically uniform and thus it can be considered as a completely new product. It has been called satietin-D.

SPECIFIC DESCRIPTION

Figure 1:
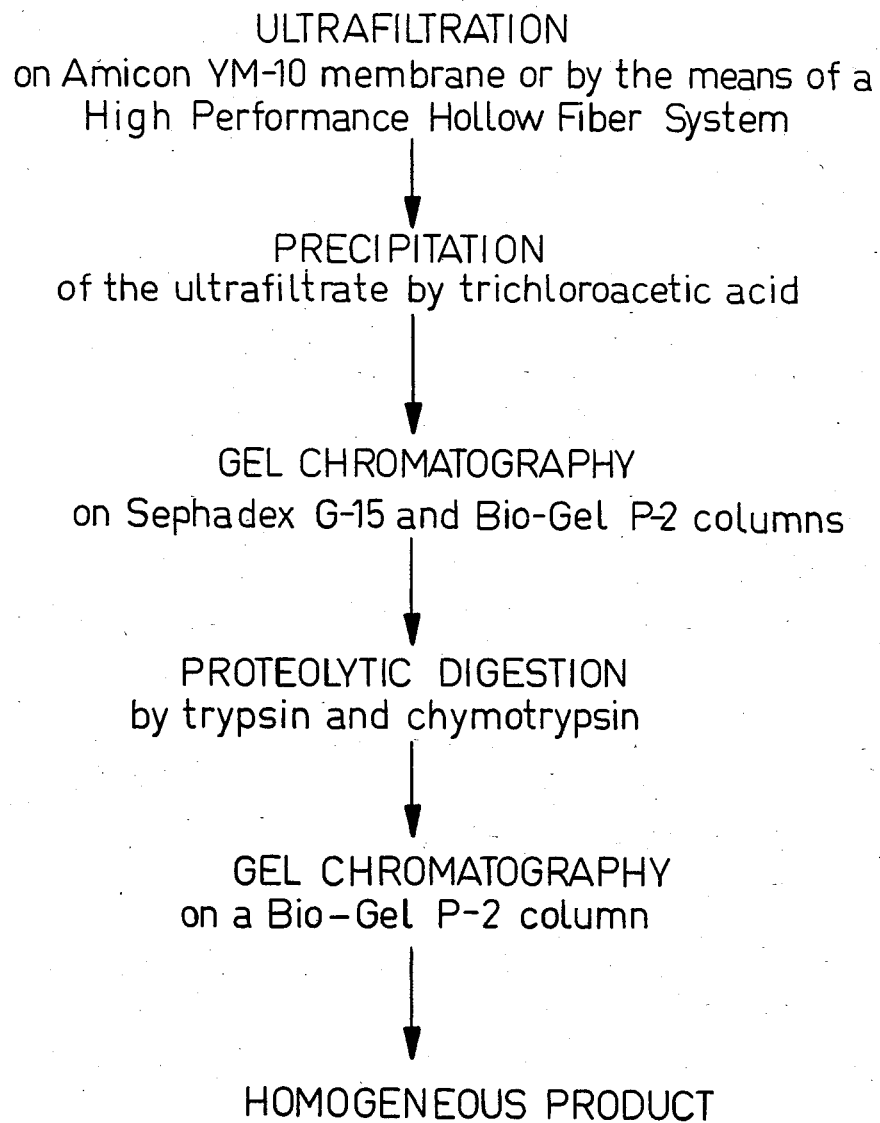
FIG. 1 is a flow diagram illustrating the process of the invention.
Figure 2:
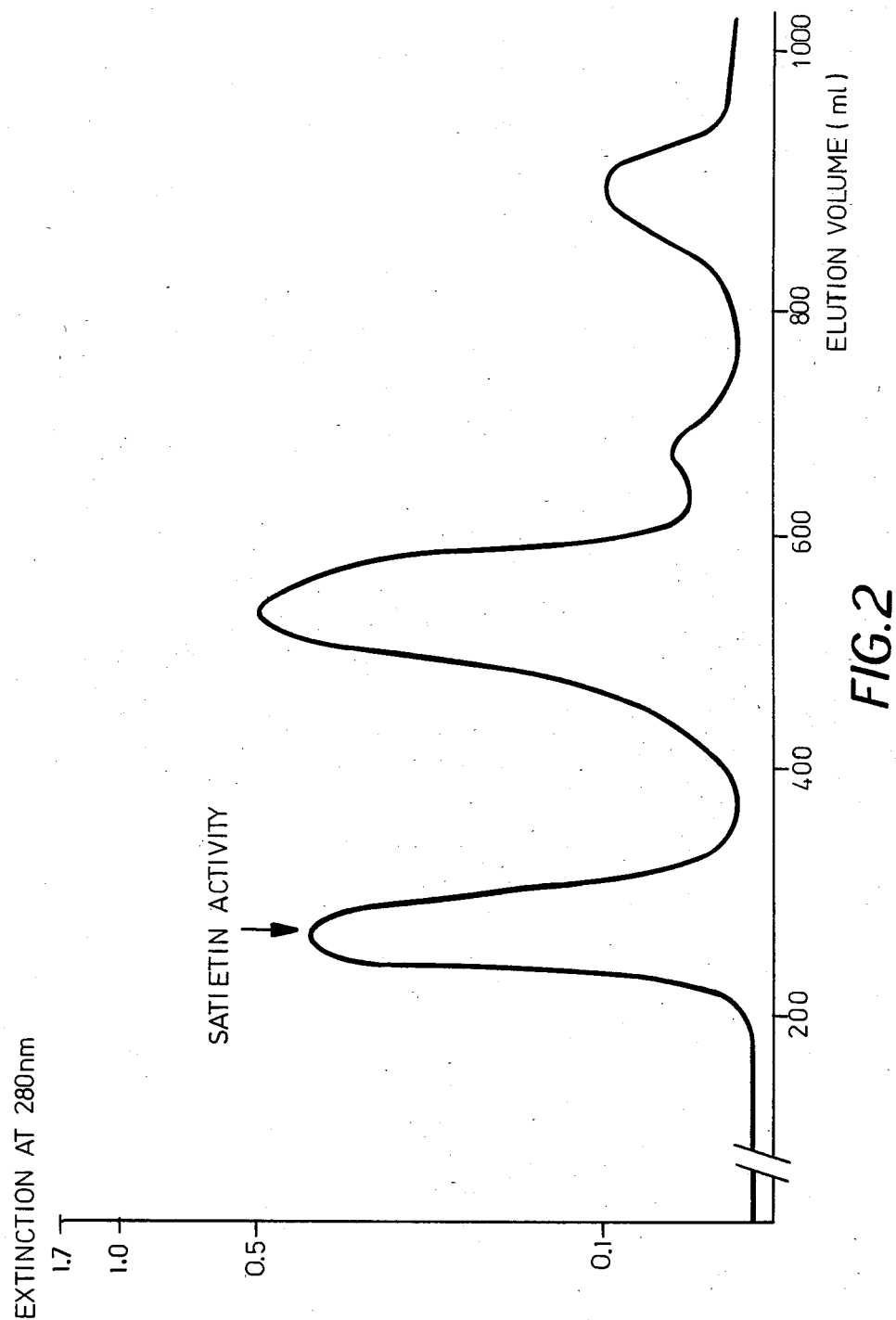
FIG. 2 is an elution diagram.

As shown in FIG. 1, the isolation process is as follows.

Blood serum or plasma deriving from humans and/or mammals is filtered through a membrane filter transmitting up to a molecular weight range of 50,000 daltons. This membrane filtration (or ultrafiltration) can be carried out through a flat membrane or a column, respectively (by the so-called "hollow-fibre" technique). Then, the filtrate is evaporated, the insoluble part is removed from the concentrate suitably by centrifuging or filtering and trichloroacetic acid is added to the liquid up to a concentration of 5 to 25 weight/volume-%, preferably 9 to 11 weight/volume-(wt./vol.)-%, at a temperature between 0° and 10° C. The precipitated proteins are suitably removed by centrifuging or filtering, the pure solution obtained is subjected to chromatography on a gel with a void volume below a molecular weight of 4000 daltons, eluted with a buffer solution of pH 6.0 to 7.0, the biologically active fractions are concentrated suitably by lyophilization or evaporation under reduced pressure, chromatographed again on a gel with a void volume below a molecular weight of 3000 to 4000 daltons, eluted with distilled water (desalted) and the crude product obtained is further purified or treated, e.g. to convert it to a lyophilized form.

According to the process of the invention, this lyophilized crude product is dissolved in a buffer solution of pH 8.1 to 8.2, suitably in an 0.1 molar solution of 2-amino-2-hydroxymethyl-1,3-propanediol hydrochloride (TRIS hydrochloride), then trypsin in a weight of 0.01 to 0.2, suitably of 0.1 parts by weight, as well as chymotrypsin in the same amount as calculated for the total weight are added. Then, the reaction mixture is subjected to digestion at 36° C. to 39° C., and preferably 37° to 38° C. for 20 to 30, suitably for 24 hours, preferably under periodical stirring or continuous shaking. After the first 5 hours, a half amount (as calculated for the former quantity) of trypsin and chymotrypsin are added to the mixture and the digestion is continued. The pure active substance is separated in a salt-free form from the mixture by a cold treatment with trichloroacetic acid and by subsequent chromatography on a gel with a void volume below a molecular weight of 3000 to 4000 daltons.

According to a practical embodiment of the process of the invention, the purifying operation is begun with an ultrafiltration on an Amicon YM-10 flat membrane or in an Amicon "hollow fiber" device on a column separating at 50,000 daltons, suitably by using a pressure or an appropriate pump. The ultrafiltrate obtained is concentrated by evaporation under reduced pressure and the insoluble part is separated on a preparative centrifuge or filtered out on a Zeiss filter-board by using reduced pressure. The thus-obtained precipitate-free mixture is cooled to a temperature between 0° and 10° C. and 55% trichloroacetic acid is added up to a concentration of 5 to 25 wt./vol.-%, preferably of 9 to 11 wt./vol.-%. The solution thus treated is kept at a temperature of 0° to 5° C. preferably for one hour, then the precipitate or turbidity, respectively, is removed at the same temperature by ultracentrifuging or by filtering through a Zeiss filter-board at reduced pressure to give a pure, sharp, yellow solution. As known from the above-cited patent specifications, the proteins, e.g. albumin present after the ultrafiltration, are also removed by the trichloroacetic acid, while the active substance, i.e. satietin, remains in the solution.

As the next step of purification, preparative gel chromatography is employed on a gel column with a void volume below a molecular weight of 4000 daltons. This step can be carried out on a column filled with Sephadex G-15, G-10 or G-25 gel. An 0.1 molar ammonium acetate solution is used for elution, as it is relatively easy to remove by lyophilization due to its volatility. In addition, physiological saline (0.9% sodium chloride solution) or various phosphate buffers may also be employed for the separation. The active fractions appear at the void volume of the column (they are excluded from the gel at an eluant volume amounting to one third of the column volume), are combined and concentrated by lyophilization.

The following step of purification also involves chromatography on a gel with a void volume below a molecular weight of 3000 daltons, suitably on a Bio-Gel P-2 column, in distilled water as medium. This purifying step results in eliminating the salts and other contaminations of lower molecular weight possibly present. The fractions bearing the satietin activity and appearing at the void volume are combined and lyophilized to give a crude product in the form of a light yellow or white powder, with an isoelectric point of pI 7.0 to 7.1. In this way, 8 to 10 mg of a lyophilized crude product are obtained from 1 liter of human serum or plasma which can be used as food intake regulating agent showing a satietin activity of 25 SU (satietin unit) per 1 milligram.

The satietin activity of the product is determined by the method elaborated by us for measuring the biological activity. One unit of satietin (SU) means an amount of the active substance which, on intracerebroventricular administration to CFY female rats weighing 200 to 240 g after 96-hour starvation, diminishes the consumption of the standard food-plug from an average of 24.4±0.76 g to 10 g in the first day of alimentation.

The so-obtained crude product bearing the satietin activity cannot yet be considered as a uniform, homogeneous product, as it shows several bands detectable by protein dying when studied by electrophoretic methods, e.g. by acrylamide gel electrophoresis in the presence of sodium dodecyl sulphate (SDS) or by isoelectric focussing.

In the course of the efforts aimed at the preparation of a uniform active substance, a more efficient and simple method, differing from the former ones, has been elaborated. In this step of the process of the invention proteolytic digestion was used, based on the consideration that the peptides and proteins occurring as contaminants are decomposed by the digestion, while satietin being a glycoprotein is much more stable against the protein digestion. Thus, according to a practical embodiment of the process of the invention, the product of high purity, obtained by means of the purifying methods edescribed above, is dissolved in a mildly alkaline buffer of pH 8.1 to 8.2, preferably in an 0.1 molar TRIS hydrochloride solution and trypsin in an amount of 0.01 to 0.2, preferably of 0.1, parts by weight as calculated for the total weight of the lyophilized product as well as an equal amount of chymotrypsine are added to the solution. Subsequently, the mixture is kept at a temperature of 36° to 39° C., preferably at 37° to 38° C., for 20 to 30, preferably for 24 hours. The reaction mixture is preferably shaken or stirred. Five hours following the start of the digestion, trypsin and chymotrypsin are added to the mixture in a half quantity as calculated for the original one and the digestion is continued. After about 24 hours, the mixture is cooled to a temperature between 0° and 10° C. and trichloroacetic acid is added up to a concentration of 4 to 6, preferably of about 5 wt./vol.-%. Then the mixture is kept between −15° and +5° C. for at least one hour and at most for 24 hours. Thereafter the precipitated insoluble parts are eliminated preferably by ultracentrifuging or by filtering through a Zeiss filter-board.

In the next step of the purification, the trichloroacetic acid, the salts, the buffer used and other fragments of low molecular weight are eliminated after removing the enzyme excess used for the digestion with trichloroacetic acid. According to the process of the invention, this is carried out by eluting the pure and clear reaction mixture, preferably with an aqueous medium on a gel having a void volume below a molecular weight of 3000 to 4000 daltons. The pure, homogeneous satietin is excluded from the gel and appears at a volume equal to one third of that of the column at elution. The fractions containing the active substance obtained by deionized water are combined and lyophilized. A snow-white, completely pure and uniform powder is obtained which is easy to handle. This is called satietin-D, being different from the homogeneous satietin product prepared previously.

The molecular weight of the uniform and pure satietin-D active substance isolated according to the process of the invention was determined by gel electrophoresis using sodium dodecyl sulphate (SDS) to result in a molecular weight between 40,000 and 50,000 daltons. The purity and uniformity of the product were also proved by the SDS gel electrophoresis indicating a single band sensitive to both protein and carbohydrate dying, a fact also showing the glycoprotein nature of the product. The isoelectric focussing of the product by developing in the presence of ampholyn of pH 3 to 10 and 3 to 5, respectively, indicated the isoelectric point to be about a pI value of 2.9 to 3.1. This value differs from the former ones and indicates a substance present in the human serum that can be considered as a new product.

The ultimate composition of this product was found to be as follows:

| | |
|---|---|
| Protein content | 20 to 23% |
| Carbohydrate content | 56 to 60% |

-continued

| Chemically unbound water content | 6 to 10%. |

The protein content was determined by the microbiuret method and by analysis of the aminoacids following hydrolysis. The analysis of the aminoacids gave the following results:

Asp 2.83%, Thr 1.61%, Ser 1.25%, Glu 3.60%, Pro 1.36%, Gly 0.87%, Ala 1.18%, Cys 0.16%, Val 0.93%, Met 0.17%, Ile 0.76%, Leu 1.25%, Phe 0.77%, Lys 3.67%, His 0.22%, Arg 0.67%. Thus the total aminoacid content was found to be 22.71% and the glucoseamine content to be 4.90%.

The distribution of the carbohydrate content is in a sample e.g. as follows:

Fucose 4.5%, mannose 8.05%, galactose 30.3%, glucose 14.4%, totally 56.5%.

It is clear and unambiguous from the above analytical data and characteristics that the product obtained by the digestion process is a new and so far unknown product which is separated from the human serum. Approximately, from 1 liter of a human serum, 4 to 6 mg of a pure and uniform product can be separated with a satietin activity of about 50 to 100 SU/mg.

SPECIFIC EXAMPLES

The process of the invention is illustrated in detail by the following non-limiting Examples.

EXAMPLE 1

(a) 3000 ml of a human serum are filtered through Amicon UM-10 membrane while constant stirring under 3 to 4 atmospheres. The obtained ultrafiltrate of about 2000 ml is evaporated to 60 ml under reduced pressure. The concentrate containing a precipitate is centrifuged with 9000 g for 30 minutes, then the supernatant liquid is separated, 12 ml of 55% trichloroacetic acid are dropped to while cooling and stirring, whereafter the mixture is kept at a temperature of 5° to 10° C. for 1 hour. For removing the precipitated proteins, the mixture is subjected to ultracentrifuging with 30,000 g at a temperature of about 5° C. until an optically quite pure supernatant liquid is obtained. This liquid is chromatographed on a Sephadex G-15 column (5.90 cm) and eluted with an 0.1 molar ammonium acetate buffer of pH 6.6. The fractions between 500 and 600 ml are combined and lyophilized. The lyophilized residue is dissolved in 10 ml of distilled water and introduced to a Bio-Gel P-2 gel column (2.5×90 cm). The column is eluted with distilled water and the fractions between 130 and 180 ml are combined and lyophilized to give 25 mg of a crude, salt-free satietin as a yellowish-white powder.

(b) A solution of a concentration of 5 mg/ml is prepared from 100 mg of the crude product (obtained as described under (a) above) in an 0.1 molar TRIS hydrochloride buffer solution of pH 8.2 by shaking or stirring at room temperature. 10 mg of trypsin and simultaneously 10 mg of chymotrypsin are added to the obtained slightly opalescent solution, then the mixture is thoroughly stirred. The mixture containing some precipitate is placed in a bath kept at 37° C. and occasionally shaken or stirred. After 5 hours, 5 mg of trypsin 5 mg of chymotrypsin are added to the mixture and the incubation at 37° C. is continued for 19 hours, i.e. the reaction mixture is incubated for a total of 24 hours. After finishing the digestion, the mixture is cooled to a temperature between 0° and 5° C., 0.1 wt./vol.-%, i.e. 2 ml of cold (about 5° C.) trichloroacetic acid of 55 wt./vol.-% are added, then the mixture is thoroughly shaken and then frozen overnight or kept at least for 1 hour at a temperature between 0° and 5° C., respectively. Thereafter, the slightly opalescent mixture occasionally containing some precipitate is subjected to ultracentrifuging with 15,000 to 20,000 g at the temperature defined above for 25 minutes. The pure supernatant is introduced to a Bio-Gel P-2 gel column (5.0×45 cm) and the column is eluted with distilled water. The fractions between 250 and 320 ml are combined and lyophilized to give 58 mg of a pure, salt-free satietin-D as a snow-white powder with a biological activity of 50 to 100 SU/mg.

EXAMPLE 2

(a) 3000 ml of a human serum are filtered through an Amicon "hollow fiber" 30,000 column by using a pressure of 3 to 4 atmospheres while constant stirring. The obtained ultrafiltrate of about 2000 ml is evaporated to 60 ml under reduced pressure. The concentrate containing a precipitate is centrifuged with 9000 g for 30 minutes, then the supernatant liquid is separated, 12 ml of 55% trichloroacetic acid are added dropwise while cooling and stirring and the mixture is kept at a temperature of 5° to 10° C. for 1 hour. The precipitated proteins are removed from the mixture by ultracentrifuging with 30,000 g at a temperature of about 5° C. until an optically quite pure supernatant liquid is obtained which is then chromatographed on a Sephadex G-15 column (5.90 cm) and eluted with an 0.1 molar ammonium acetate buffer solution of pH 6.6. The fractions between 500 and 600 ml are combined and lyophilized. The lyophilized residue is dissolved in 10 ml of distilled water and introduced to a Bio-Gel P-2 gel column (2.5×90 cm). The column is eluted with distilled water, the fractions between 130 and 180 ml are combined and lyophilized to give 30 mg of a crude, salt-free satietin as a yellowish-white powder.

(b) A solution of a concentration of 5 mg/ml is prepared from 100 mg of the crude product (obtained as described under (a) of Example 2) in an 0.1 molar TRIS hydrochloride buffer solution of pH 8.2 by shaking or stirring at room temperature. 10 mg of trypsin and simultaneously 10 mg of chymotrypsin are added to the obtained slightly opalescent solution, then the mixture is thoroughly stirred. The mixture containing some precipitate is placed in a bath kept at 37° C. and occasionally shaken or stirred. After 5 hours, 5 mg of trypsin and 5 mg of chymotrypsin are added to the mixture and the incubation at 37° C. is continued for 19 hours, i.e. the reaction mixture is incubated for a total of 24 hours. After finishing the digestion, the mixture is cooled to a temperature between 0° and 5° C., 0.1 vol./vol.-%, i.e. 2 ml, of cold (about 5° C.) trichloroacetic acid of 55 wt./vol.-% are added, then the mixture is thoroughly shaken and then frozen overnight or kept at least for 1 hour at a temperature between 0° and 5° C., respectively. Thereafter, the slightly opalescent mixture occasionally containing some precipitate is subjected to ultracentrifuging with 15,000 to 20,000 g at the temperature defined above for 24 minutes. The pure supernatant is introduced to a Bio-Gel P-2 gel column (5.0×45 cm) and the column is eluted with distilled water. The fractions between 250 and 320 ml are combined and lyophilized to give 62 mg of a pure, snow-white, salt-free satietin-D with a biological activity of 50 to 100 SU/mg.

What we claim is:

1. A process for isolating a food intake suppressant from human or animal blood serum which comprises subjecting the human and/or animal blood serum to ultrafiltration on a membrane or hollow fiber ultrafilter passing a filtrate containing substances of a molecular weight of at most 50,000 daltons, partially evaporating the filtrate, removing the insoluble part from the concentrate obtained, adding trichloroacetic acid up to a concentration of 5 to 25 weight/volume percent to the liquid phase at a temperature of 0° C. to 10° C., removing the proteins precipitated, subjecting the obtained solution to chromatography on a gel with an elution solution of pH 6.0 to 7.0, concentrating the biologically active fractions, chromatographing again on a gel with a void volume having a molecular weight of 3000 to 4000 daltons, fractionating by elution with water, lyophilizing the active fractions, dissolving the lyophilized fractions in a buffer of pH 8.1 to 8.2, adding trypsin and chymotrypsin to the solution in substantially identical amounts of 0.01 to 0.2 by weight as calculated for the total weight of the lyophilized product, subjecting the mixture to digestion at a temperature of 36° C. to 39° C. for 20 to 30 hours, adding after the first 5 hours an equal quantity of trypsin and chymotrypsin in a substantially half amount as calculated for the original enzyme quantity and continuing the digestion, then adding trichloroacetic acid to the reaction mixture up to a concentration of 4 to 6 weight/vol. % at a temperature between 0° C. and 10° C., keeping the mixture at a temperature between $-15°$ C. and 5° C. for 1 to 24 hours, removing the insoluble part, subjecting the reaction mixture to chromatography on a gel with a void volume having a molecular weight of 3000 to 4000 daltons, fractionating by elution with water and lyophilizing the biologically active fractions to yield said food intake suppressant having a molecular weight between 40,000 and 50,000 daltons.

2. A process as claimed in claim 1, which comprises carrying out the ultrafiltration of the human or animal blood serum through a flat membrane.

3. A process as claimed in claim 1, which comprises carrying out the ultrafiltration of the human or animal blood serum on a column.

4. A process as claimed in claim 1, which comprises removing the insoluble parts or the precipitated proteins by ultracentrifuging or filtering under reduced pressure.

5. A process as claimed in claim 1, which comprises eluting with an 0.1 molar ammonium acetate solution as a buffer solution of a pH value between 6.0 and 7.0.

6. A process as claimed in claim 1, which comprises concentrating the biologically active fractions by lyophilization or evaporation under reduced pressure after eluting with the solution of a pH value between 6.0 and 7.0.

7. A process as claimed in claim 1, which comprises using an 0.1 molar solution of 2-amino-2-hydroxymethyl-1,3-propanediol hydrochloride as a buffer solution of a pH value between 8.1 and 8.2.

8. A process as claimed in claim 1, which comprises adding to the solution trypsin and chymotrypsin in an identical amount of 0.1 by weight as calculated for the total weight of the lyophilized product.

9. A process as claimed in claim 1, which comprises carrying out the digestion at a temperature of 37° C. to 38° C. for 24 hours.

* * * * *